United States Patent [19]

Carlson

[11] Patent Number: 4,642,052
[45] Date of Patent: Feb. 10, 1987

[54] DENTURE WITH CHEWING INSERTS

[76] Inventor: Robert D. Carlson, 306 Walnut Ave., #39, San Diego, Calif. 92103

[21] Appl. No.: 782,876

[22] Filed: Oct. 2, 1985

[51] Int. Cl.⁴ ............................................. A61C 13/00
[52] U.S. Cl. .................................................... 433/189
[58] Field of Search ........................................... 433/198

[56] References Cited

U.S. PATENT DOCUMENTS

| | | | |
|---|---|---|---|
| 2,295,864 | 9/1942 | Prange | 32/8 |
| 2,300,577 | 11/1942 | La Due et al. | 32/8 |
| 2,375,509 | 5/1945 | Wiechert | 32/8 |
| 2,397,407 | 3/1946 | Butler | 32/8 |
| 2,717,445 | 9/1955 | Ford | 32/8 |
| 2,935,791 | 5/1960 | Adams | 32/2 |
| 2,941,295 | 6/1960 | Jermyn | 433/198 |
| 4,031,623 | 6/1977 | Levin | 32/8 |

Primary Examiner—Robert Peshock
Attorney, Agent, or Firm—Brown, Martin, Haller & Meador

[57] ABSTRACT

A denture includes an upper and lower row of teeth, with a continuous chewing bar embedded along the buccal cusps of at least part of the lower row. Insert members are embedded in the opposed occlusal faces of teeth in the upper row, and are shaped to form arches or indents against which the chewing bar travels on articulation of the denture to create a scissors action.

15 Claims, 13 Drawing Figures

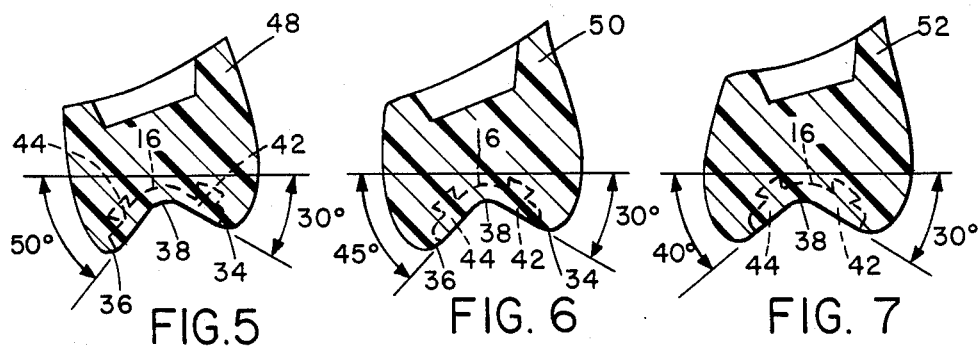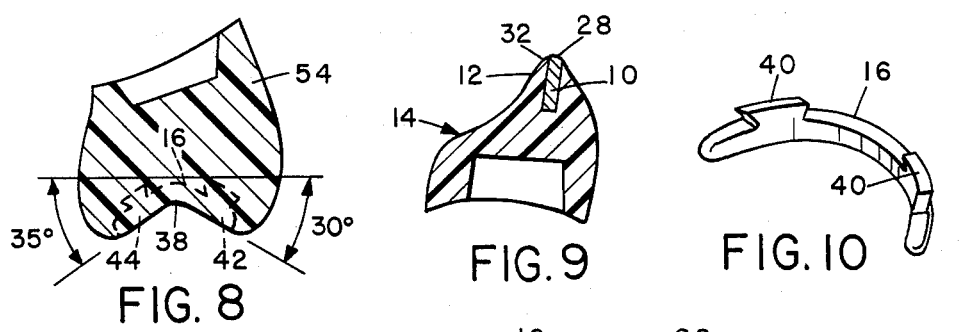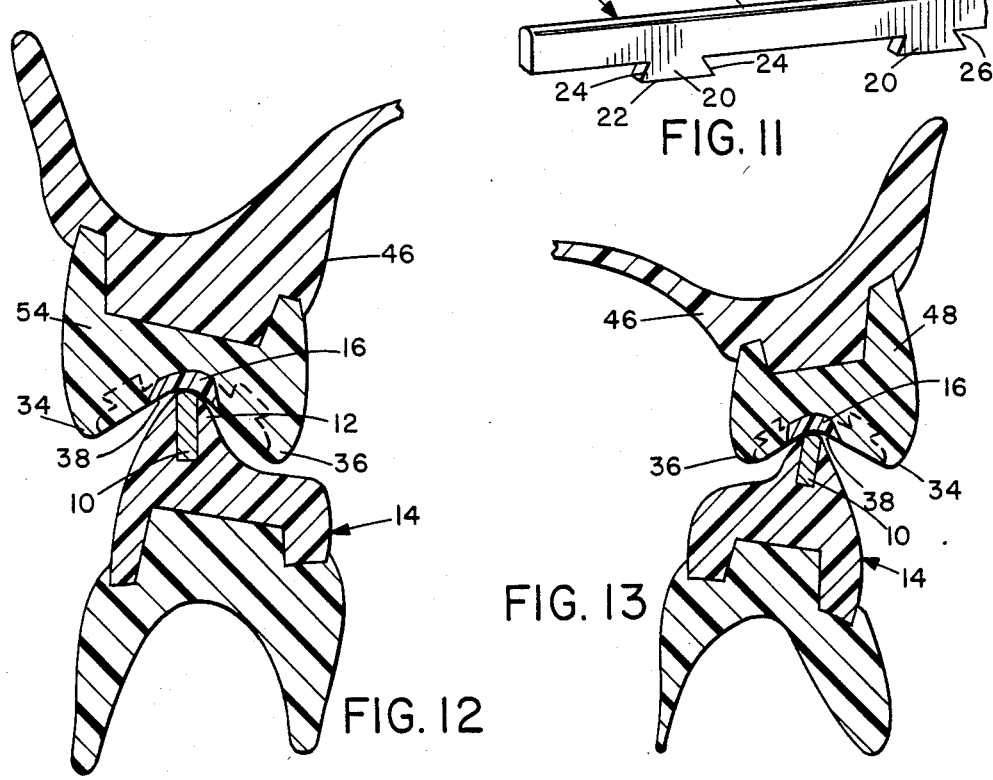

4,642,052

DENTURE WITH CHEWING INSERTS

BACKGROUND OF THE INVENTION

The present invention relates to inserts for dentures to aid in chewing, and to reduce wear of the denture and discomfort to denture wearers.

The wearers of dentures often have problems in chewing certain foods, and also complain of the development of sore spots on their gums due to movement of the dentures on chewing food. The laboratory set up of standard dentures to reduce these problems is difficult, involving the balancing of teeth individually on an articulator. Dentures normally have many ridges, cusps and fossae, and to balance all ridges in their proper fossae is a very difficult task. When the dentist fits the dentures, he must additionally attempt to balance the dentures in all functional movements when they are placed in the mouth. Improper balancing results in the development of sore spots and makes chewing more difficult. Additionally, ridges will tend to be absorbed more rapidly and the dentures will be apt to click together, adding to the discomfort of the wearer.

Hard inserts for dentures to aid in chewing are shown, for example, in U.S. Pat. No. 2,941,295 of Jermyn, in which upper and lower opposed chewing bars are embedded in the upper and lower plates of a denture. U.S. Pat. No. 4,031,623 of Levin shows bladed inserts in artificial teeth for cutting and shearing food.

SUMMARY OF THE INVENTION

According to the present invention, a denture is provided which includes an upper and a lower row of teeth, a continuous insert bar embedded along at least part of the lower row of teeth so as to form the apex of the buccal cusp of each tooth through which it extends, and arched insert members embedded in the occlusal faces of opposed teeth in the upper row so as to interact with the insert bar to create a scissors action when the wearer of the denture chews food.

In the preferred embodiment of the invention, an insert bar is embedded in at least some of the bicuspid and molar teeth on one or both sides of a denture. The denture may be a full or partial plate. The occlusal faces of the bicuspid and molar teeth in the upper row opposing the chewing bar are shaped to form an indent or fossa in which the chewing bar rotates on chewing food, providing a scissors or cutting action to aid in masticating. The insert members in the upper teeth form at least part of the opposed indented surface against which the chewing bar articulates. In one preferred example, the insert members are arranged in opposed pairs, with at least one pair of insert members embedded in each of the teeth facing the chewing bar. Each member is suitably curved or substantially V-shaped, and is embedded in a respective tooth so as to face the opposing member of the pair and to follow the indented surface of the occlusal face of the tooth. The upper molar teeth suitably have two pairs of insert members embedded in their occlusal faces, one pair in each segment.

The provision of a continuous straight chewing or insert bar will minimize or substantially reduce movement of the denture on chewing, and by suitable angling of the opposed indented surfaces of the upper teeth and/or insert member to follow the rotational movement of the insert bar on chewing, balancing of the denture will be much easier to achieve.

In one preferred embodiment of the invention, the angle of the lingual cusp of the upper teeth opposing the insert bar to the horizontal plane of occlusion decreases with distance away from the condyle, to allow for the increase in jaw movement with distance away from the pivot point.

BRIEF DESCRIPTION OF THE DRAWINGS

The present invention will become more clear from the following detailed description of a preferred embodiment of the invention, taken in conjunction with the accompanying drawings in which like reference numerals refer to like parts and in which:

FIG. 5 is a vertical cross section on the lines 5—5 of FIG. 1 through the upper second molar of the row of teeth in FIG. 1;

FIG. 6 is a vertical cross-section on the lines 6—6 of FIG. 1 showing an insert in the upper first molar;

FIG. 7 is a vertical cross-section on the lines 7—7 of FIG. 1 showing an insert in the second bicuspid;

FIG. 8 is a vertical cross-section on the lines 8—8 of FIG. 1 showing an insert in the first bicuspid;

FIG. 9 is a vertical cross-section on the lines 9—9 of FIG. 3 showing the insert bar in one of the lower teeth;

FIG. 10 is a perspective view of one of the upper tooth inserts;

FIG. 11 is a perspective view of the lower teeth insert bar;

FIG. 12 is a vertical section through an upper and lower molar tooth of a denture showing the engagement between the upper and lower tooth inserts; and FIG. 13 is a vertical section similar to FIG. 12 through an upper and lower bicuspid tooth.

DESCRIPTION OF THE PREFERRED EMBODIMENT

Figure 1:
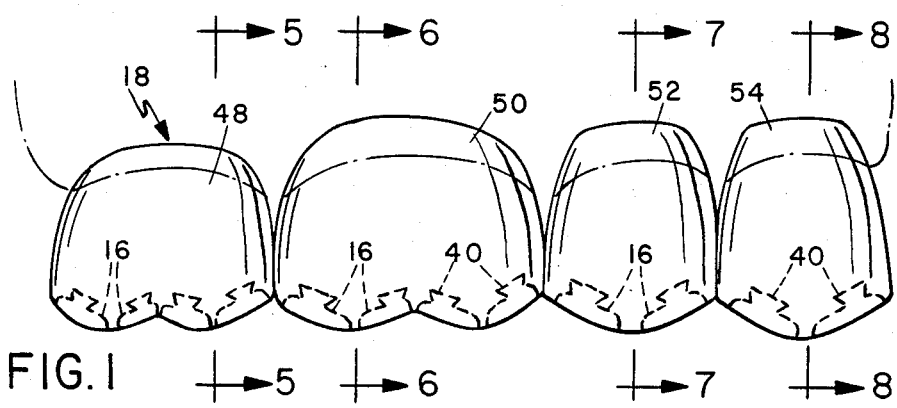
FIG. 1 is a front elevational view of an upper row of teeth in a denture incorporating upper tooth inserts according to a preferred embodiment of the present invention.

FIGS. 1 to 4 of the drawings show upper and lower rows of teeth in a denture with chewing inserts according to a preferred embodiment of the present invention. Although four upper and lower teeth are shown in the denture, this may be part of a full or partial denture or a complete partial denture. The invention may be used in dentures having a greater or lesser number of teeth, for example in any full or partial plate denture. The teeth may be set in a group as shown, or individually.

The denture inserts according to the invention basically comprise a lower continuous chewing bar 10 embedded in the buccal cusps 12 of the lower teeth 14, and pairs of curved insert members 16 embedded in the opposed occlusal faces of the upper teeth 18 so as to interact with the chewing bar during chewing of food. The insert bar 10 and insert members 16 are shown in more detail in FIGS. 10 and 11.

The lower chewing bar 10 and upper insert members are of a harder material than the surrounding acrylic denture material, and may be of a plastics material suitable for dental use, or of sapphire, for example. The chewing bar 10 provides a scissors action relative to each upper tooth as the false teeth rotate during normal jaw motion on masticating food. The interaction between the lower chewing bar and the upper insert members improves chewing efficiency.

Figure 3:
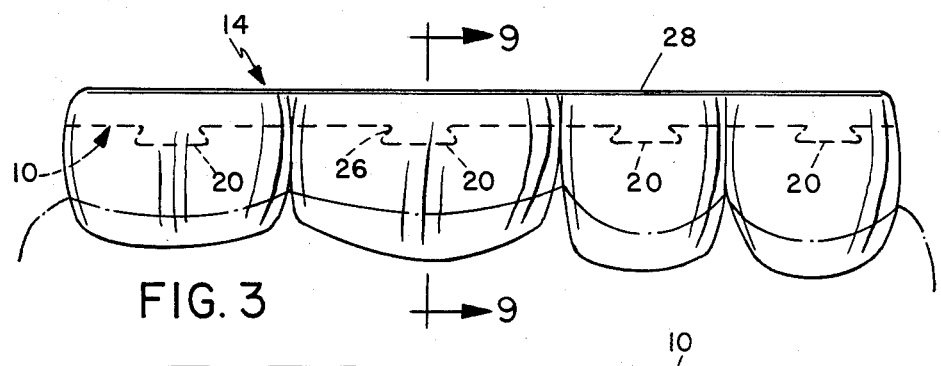
FIG. 3 is a front elevational view of the lower row of teeth in a denture incorporating a lower tooth insert bar according to the preferred embodiment of the invention.
Figure 4:
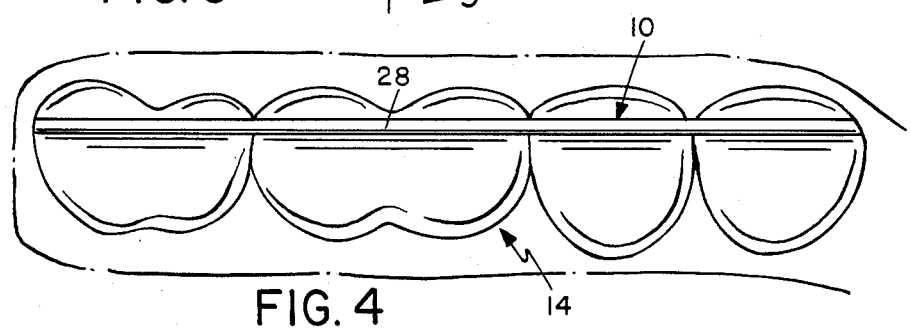
FIG. 4 is a top plan or occlusal view of the row of teeth shown in FIG. 3.

As best shown in FIGS. 3, 4, 9 and 11, the chewing or insert bar 10 is a substantially straight bar which has a series of projections or castellations 20 along its lower edge. The projections 20 have flat lower edges 22 and indented or tapered side edges 24. Each projection is designed to be embedded in a respective one of the row of teeth along which the bar is mounted, as shown in FIG. 3, and acts as an anchor for positively holding the bar in the tooth because of the denture material embedded in the indents 26 defined by the tapered side edges 24 of the projection 20. The projections may have holes to aid in anchoring the bar in place.

The upper edge 28 of the bar 10 is rounded, and each of the lower teeth in which it is embedded is narrowed or pointed towards the buccal cusp 12 in the bucco-lingual direction, as shown in FIG. 9, so that the cusps with the embedded bar 10 tend towards a rounded apex or point 32.

Figure 2:
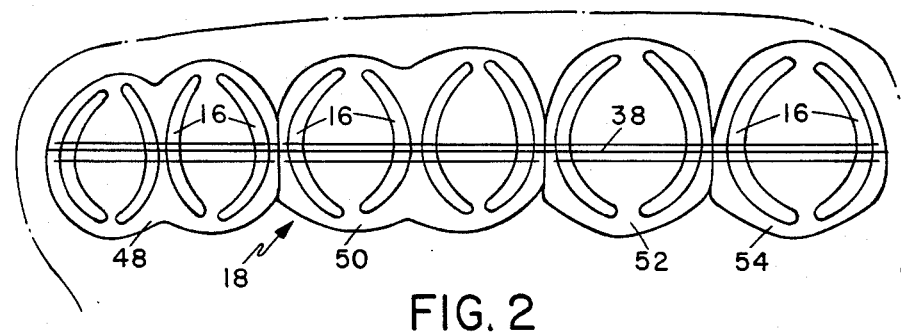
FIG. 2 is a bottom plan or occlusal view of the row of teeth shown in FIG. 1.

Each of the upper teeth 18 of the denture is arched between its buccal, or cheek-facing cusp 34 and its lingual, or tongue-facing cusp 36 to define an indent or fossa 38 on the occlusal face of the tooth which mates or cooperates with the opposed buccal cusps of the lower teeth (see FIGS. 12 and 13). The insert members 16 are arranged in pairs facing one another on the occlusal faces of each upper tooth, as best shown in FIG. 1, so as to form part of the indented surface mating with the lower chewing bar 10. Each bicuspid tooth has one pair of insert members and each molar has two pairs, one in each segment of the molar, as shown in FIG. 2.

As best shown in FIG. 10, each insert member 16 is arched or substantially V-shaped and has projections or anchors 40 along its upper edge, similar to the projections 20 on the insert bar 10, for anchoring it in the tooth. Each insert member is embedded in a respective upper tooth so that its curve follows the curve of the arch or fossa 38 of the occlusal face of that tooth, with one arm or limb 42 lying along the buccal cusp of the tooth and the other arm or limb 44 lying along the lingual cusp of the tooth, as seen in FIG. 5 to 8.

The limbs of each insert member are embedded so as to be inclined inwardly towards the opposite member of the pair, and downwardly relative to the horizontal plane of occlusion. As can be seen in FIG. 2, the pairs of insert members substantially follow the outer contour of the occlusal face of the tooth or tooth segment in which they are embedded. They may project slightly from the occlusal face of the tooth, but are preferably flush with it as shown in the drawings.

Instead of pairs of insert members as shown, a single, curved plate-like insert member may be used to comprise part or all of the opposed occlusal face of the upper tooth, so that the insert bar acts continuously against the harder material of the opposed insert members.

FIGS. 12 and 13 show the engagement between the lower insert bar 10 and upper insert members 16 in a denture 42. The bar engages in the indent or arch 38 defined by the insert members and occlusal faces of the upper row of teeth. The bar will have an incising effect on food trapped between the bar and insert members, and will articulate against the insert members to create travelling points in a scissor's-like action to improve chewing efficiency.

The occlusal faces of upper teeth of the denture and the inserts in the upper teeth are angled to agree with the travel of the insert bar 10 on articulation so that it tends to maintain contact with them during its travel. The angle of travel will increase gradually with distance away from the condyle or hinge point of the jaw, so by angling the upper teeth to agree with this change in angle, cross-mouth balance of the denture will be much easier to achieve.

The change in angle on the lingual cusps of the upper teeth from the second molar to the 1st bicuspid can be seen in FIGS. 5 to 8. On average, every 2 mm of distal measurement should add about 1° of angle to the upper lingual cusps, i.e. about 5° change per tooth. If the distal second molar 48 is 30 mm from the mesial first bicuspid, the lingual cusp of the second molar is about 50° from the horizontal plane of occlusion, as shown in FIG. 5. The lingual cusp of the first molar 50 is about 45° (See FIG. 6), the second lingual cusp of the second bicuspid 52 is about 40°, and the lingual cusp of the first bicuspid 54 is about 35°. All angles measured relative to the horizontal plane of occlusion. The insert members 16 for these teeth are arranged to correspond to these angles in their lingual arms 44 when embedded at the correct orientation in the respective teeth.

The buccal cusps of the upper teeth are all angled at about 30° with the buccal arms 42 of the insert members 16 being at the same angle so that they follow the curve of the buccal cusp of the tooth in which they are embedded. This angle will allow separation of the anterior teeth when chewing. This allows a proper aesthetic over-bite and over-jut of the anterior teeth.

In FIG. 12, the engagement between the chewing bar 10 and one of the upper insert members 16 in opposed bicuspid teeth during part of a chewing action is shown. A similar interaction between opposed molar teeth is shown in FIG. 13.

Because of the arrangement of the straight, continuous chewing bar 10 in the lower teeth of the denture, movement of the dentures when the teeth are brought together in functional or centric movements will be reduced or minimized. The chewing bar 10 will articulate with the upper insert members 16 for improved chewing efficiency, and the inserts will be self-sharpening because they are of harder material than the surrounding acrylic, for example hard plastic or sapphire.

Balancing of the dentures both in the laboratory and when they are placed in the mouth by a dentist will be easier, because the denture will already be in one piece with the correct angular set up of the occlusal faces of the upper teeth relative to the buccal cusp and insert bar of the lower teeth. Thus there is no need for balancing teeth individually on an articulator so that each ridge or cusp is correctly balanced in its proper fossa. Functional balancing of the teeth in the denture is already allowed for by the continuous chewing bar and by the changing angle of the lingual cusps of the upper teeth.

The curved apex or point 32 of the lower teeth will have an incising effect on a bolus of food, and the narrowed cusp will further ease the passage of the cusp through the bolus of food.

The wear of the teeth in this denture should be less than average because of the hardness of the lower insert bar and upper insert members. Sore spots will be less likely to occur since there will be less movement of the denture on chewing.

The teeth in the denture are balanced to provide continuous correct impact between the upper and lower teeth, making it easier for the laboratory technician to set the teeth in the dentures, and reducing movement of the dentures in the mouth.

The denture may be a full or partial plate, with corresponding insert bars and insert members embedded in the opposing faces of some or all of the molar and bicuspid teeth on each side of the mouth.

Although a preferred embodiment of the invention has been described above by way of example, it will be understood by those skilled in the field that modifications may be made to the disclosed embodiments which are within the scope of the invention as defined by the appended claims.

I claim:

1. A denture comprising:
    an upper and a lower row of artificial teeth having opposed occlusal faces, the opposed occlusal faces of at least a portion of the teeth being shaped to have buccal cusps in the lower row and cooperating indented surfaces in the upper row for cooperation with said buccal cusps on articulation of the denture;
    a continuous insert bar of material harder than that of the artificial teeth embedded in the buccal cusps along at least part of the lower row of teeth so as to form the apex of each buccal cusp through which it extends; and
    a plurality of insert members of material harder than that of the artificial teeth embedded in the occlusal faces of the upper teeth in the row opposing the insert bar, each insert member forming at least part of the indented surface of the tooth in which it is embedded so as to interact with the insert bar on articulation of the denture;
    the insert members comprising curved members arranged in opposed pairs, at least one pair of insert members being embedded in each tooth opposing the insert bar so that they form an arch following the indented surface on the occlusal face of that tooth, the limbs of each insert member being inclined inwardly towards the opposed member of that pair and downwardly relative to the horizontal plane of occlusion.

2. The denture as claimed in claim 1, in which the insert bar and insert members are embedded in at least some of the bicuspid and molar teeth of the denture.

3. The denture as claimed in claim 2, in which the denture includes bicuspid and molar teeth on each side of the mouth, and an insert bar and opposed insert members are embedded in said bicuspid and molar teeth on each side of the mouth.

4. The denture as claimed in claim 1, in which the insert members are flush with the occlusal surface of the tooth in which they are embedded.

5. The denture as claimed in claim 1, in which the buccal cusps of the lower teeth in which the insert bar is embedded are narrowed bucco-lingually towards the apex to tend towards a point.

6. A denture comprising:
    an upper and a lower row of artificial teeth having opposed occlusal faces, the opposed occlusal faces of at least a portion of the the teeth being shaped to have buccal cusps in the lower row and cooperating indented surfaces in the upper row for cooperation with said buccal cusps on articulation of the denture;
    a continuous insert bar of material harder than that of the artificial teeth embedded in the buccal cusps along at least part of the lower row of teeth so as to form the apex of each buccal cusp through which it extends; and
    a plurality of insert members of material harder than that of the artificial teeth embedded in the occlusal faces of the upper teeth in the row opposing the insert bar, each insert member forming at least part of the indented surface of the tooth in which it is embedded so as to interact with the insert bar on articulation of the denture;
    the indented surfaces of the occlusal faces of the teeth in the upper row opposing the insert bar being defined between buccal and lingual cusps of said teeth, with the angle of the lingual cusp of the opposing upper teeth to the horizontal plane of occlusion decreasing with distance away from the condyle end of the denture so as to agree with the travel fo the insert bar on articulation of the denture.

7. The denture as claimed in claim 6, in which each insert member is of arched shape having a lingual limb and a buccal limb angled to conform to the angle of the lingual and buccal cusps, respectively, of the tooth in which it is embedded.

8. The denture as claimed in claim 7, in which the insert members are arranged in pairs facing one another substantially following the outer contour of the tooth in which they are embedded.

9. The denture as claimed in claim 8, wherein the limbs of the insert members are inclined downwardly to follow the curve of said buccal and lingual cusps.

10. The denture as claimed in claim 9, in which the row of teeth includes bicuspid and molar teeth, each bicuspid tooth in the upper row having one pair of insert members embedded in its occlusal face and each molar tooth in the upper row having two pairs of insert members embedded in its occlusal face.

11. The denture as claimed in claim 6, in which the angle of the lingual cusps increases about 1 degree with each 2 mm of distal movement.

12. The denture as claimed in claim 11, in which the upper row of teeth includes the first and second bicuspid and first and second molar teeth, the lingual cusp angle of these teeth to the horizontal plane of occlusion being approximately 35°, 40°, 45° and 50°, respectively.

13. The denture as claimed in claim 6 in which the buccal cusps of said opposing upper teeth are all angled at about 30° to the horizontal plane of occlusion.

14. A denture comprising:
    an upper and a lower row of artificial teeth having opposed occlusal faces, the opposed occlusal faces of at least a portion of the the teeth being shaped to have buccal cusps in the lower row and cooperating indented surfaces in the upper row for cooperation with said buccal cusps on articulation of the denture;
    a continuous insert bar of material harder than that of the artificial teeth embedded in the buccal cusps along at least part of the lower row of teeth so as to form the apex of each buccal cusp through which it extends; and
    a plurality of insert members of material harder than that of the artificial teeth embedded in the occlusal faces of the upper teeth in the row opposing the insert bar, each insert member forming at least part of the indented surface of the tooth in which it is embedded so as to interact with the insert bar on articulation of the denture;

each insert member being of arched shape having a lingual limb and a buccal limb angled downwardly relative to the horizontal plane of occlusion to conform to the angle of the lingual and buccal cusps, respectively, of the tooth in which it is embedded.

15. The denture as claimed in claim 14, in which the insert members are arranged in opposed pairs in each tooth opposing the insert bar, the limbs of each insert member of a pair being inclined inwardly towards the opposed insert member of that pair.

* * * * *